(12) United States Patent
Noda et al.

(10) Patent No.: US 6,327,891 B1
(45) Date of Patent: Dec. 11, 2001

(54) GAS SENSOR

(75) Inventors: Keiichi Noda; Kazuo Taguchi, both of Aichi; Hisaharu Nishio, Fukishima-machi; Katsuhisa Yabuta, Aichi, all of (JP)

(73) Assignee: NGK Spark Plug Co., LTD, Aichi (JP)

( * ) Notice: Subject to any disclaimer, the term of this patent is extended or adjusted under 35 U.S.C. 154(b) by 0 days.

(21) Appl. No.: 09/257,513

(22) Filed: Feb. 25, 1999

(30) Foreign Application Priority Data

Feb. 26, 1998 (JP) .................................................. 10-064348

(51) Int. Cl.[7] .................................................. G01N 27/04
(52) U.S. Cl. ........................ 73/31.05; 73/23.31; 73/866.5; 204/424
(58) Field of Search ................................... 73/23.2, 866.5, 73/23.31, 25.05, 24.06, 31.05, 31.06; 204/424

(56) References Cited

U.S. PATENT DOCUMENTS

| | | | |
|---|---|---|---|
| 5,228,975 | 7/1993 | Yamada et al. | 204/424 |
| 5,467,636 | * 11/1995 | Thompson et al. | 73/23.31 |
| 5,616,825 | * 4/1997 | Achey et al. | 73/23.31 |
| 5,880,353 | 3/1999 | Graser et al. | 73/23.2 |
| 5,886,248 | * 3/1999 | Paulus et al. | 73/23.31 |
| 5,948,963 | * 9/1999 | Kato et al. | 73/23.2 |

FOREIGN PATENT DOCUMENTS

| | | |
|---|---|---|
| 196 05 290 A1 | 8/1997 | (DE) . |
| 196 28 423 A1 | 9/1997 | (DE) . |
| 197 05 402 A1 | 1/1998 | (DE) . |
| 197 07 459 A1 | 8/1998 | (DE) . |
| 9-257745 | 10/1997 | (JP) . |
| PCTWO 97/29364 | 8/1997 | (WO) . |

* cited by examiner

Primary Examiner—Hezron Williams
Assistant Examiner—Michael Cygan
(74) Attorney, Agent, or Firm—Brinks Hofer Gilson & Lione (57) ABSTRACT

A gas sensor has a structure in which an insulator is disposed inside a metallic shell, and a sensor element is disposed inside the insulator. A cavity is formed in the insulator to surround the sensor element. A sealing material mainly formed of glass is charged into the cavity in order to establish sealing between the inner surface of the insulator and the outer surface of the sensor element. The sensor element has a rectangular cross section, and the inner surface of the insulator defining the cavity has a sectional profile corresponding to the sectional profile of the sensor element.

5 Claims, 11 Drawing Sheets

GAS SENSOR

BACKGROUND OF THE INVENTION

1. Field of the Invention

The present invention relates to a gas sensor for detecting a component of a gas to be measured (hereinafter referred to as a measurement gas), such as an oxygen sensor, an HC sensor, an $NO_x$ sensor, or a like sensor.

2. Description of Related Art

Conventionally, there has been known a gas sensor is having a structure in which an insulator is disposed inside a metallic shell; a sensor element is disposed inside the insulator; and a sealing layer is formed between the inner surface of the insulator and the outer surface of the sensor element from a sealing material such as glass. The sealing layer is formed through charging of the sealing material into a cavity that is formed in the insulator around the sensor element.

Figure 14A:
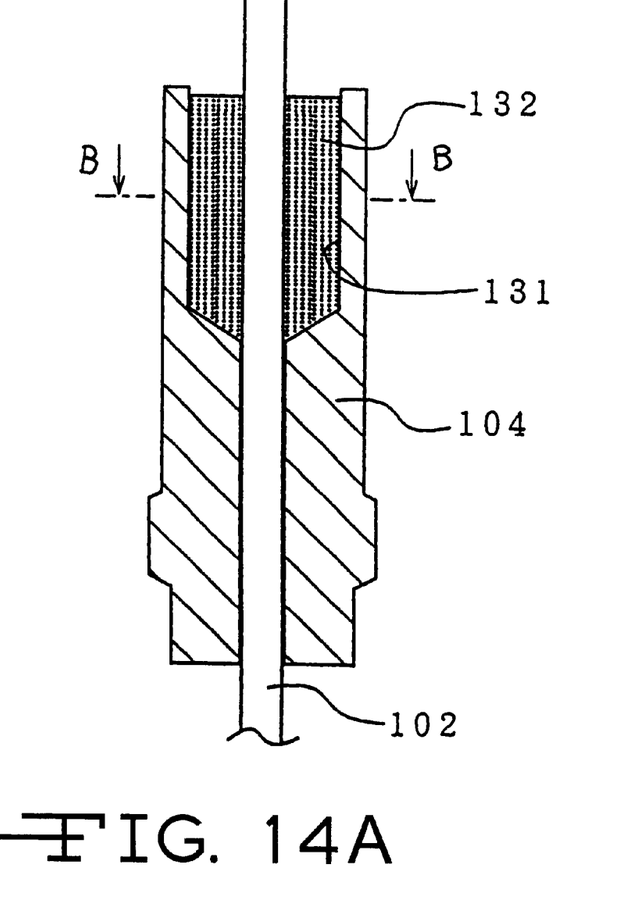
FIG. 14(a) is a longitudinal, sectional view of a main portion of a conventional gas sensor.
Figure 14B:
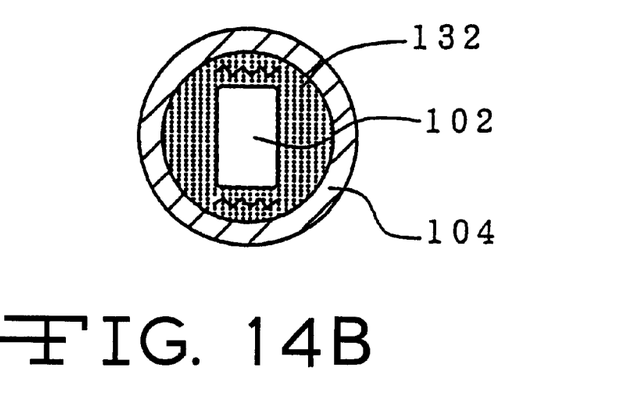
FIG. 14(b) is a transverse, sectional view showing a main portion of a conventional gas sensor taken along line B—B of FIG. 14(a).

In gas sensors having the above-described structure, the sensor element is frequently formed into a ceramic layered element. In such a case, as shown in FIG. 14, there is generally used a sensor element 102 having a rectangular cross section. However, a cavity portion 131 (i.e., a sealing material layer 132) formed in an insulator 104 conventionally has a circular cross section. This results in a structure in which the sealing material layer 132 having a circular cross section encloses the sensor element 102 having a rectangular cross section. Therefore, the thickness of the sealing material layer naturally becomes uneven such that the thickness is greater at portions corresponding to the longer sides of the cross section of the sensor element 102, and smaller at portions corresponding to the shorter sides of the cross section of the sensor element 102. For example, an oxygen sensor for automobile use is often mounted at a location, such as an exhaust manifold or an exhaust pipe located near a suspension system and tires, where the sensor may be exposed to high temperature or subjected to a strong thermal shock. When the sealing material layer 132 has an uneven thickness as described above, thermal stresses tend to concentrate at thin wall portions, resulting in the problem of shortening the life of the sealing material layer 132.

An object of the present invention is to provide a gas sensor in which the effect of thermal stress on a sealing-material layer is mitigated and which therefore has excellent durability.

SUMMARY OF THE INVENTION

A gas sensor of the present invention has the following structure. An insulator is disposed inside a metallic shell, and a sensor element for detecting a component of a gas to be measured is disposed inside the insulator. A cavity is formed in the insulator to surround the sensor element and a sealing material mainly made of glass is charged into the cavity in order to establish sealing between the inner surface of the insulator and the outer surface of the sensor element. In order to achieve the above described object, in accordance with a first aspect of the present invention, an inner surface of the insulator that defines the cavity (hereinafter referred to as a "cavity defining inner surface") has a sectional profile that conforms to that of the sensor element, when the sectional profile of the sensor element is square, rectangular, or elliptical.

In the case where the sensor element has a square, rectangular or elliptical cross section, a sealing material layer of uniform thickness can be formed around the sensor element if the cavity defining inner surface; i.e., the outer circumference of the sealing material layer charged into the cavity, has a sectional profile that conforms to that of the sensor element. By virtue of this structure, there can be prevented concentration of stresses at a thin wall portion, which has arisen in conventional gas sensors in which a sealing material layer of a circular cross section is formed around a sensor element of, for example, a rectangular cross section. Thus, the durability of the sealing-material layer can be improved.

Figure 3A:
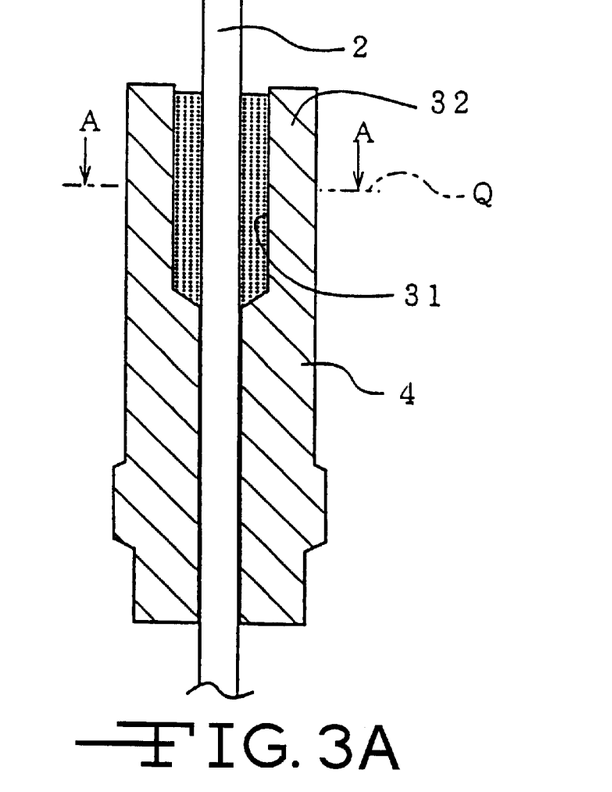
FIG. 3(a) is a longitudinal, sectional view showing a main portion of the oxygen sensor of FIG. 1.
Figure 3B:
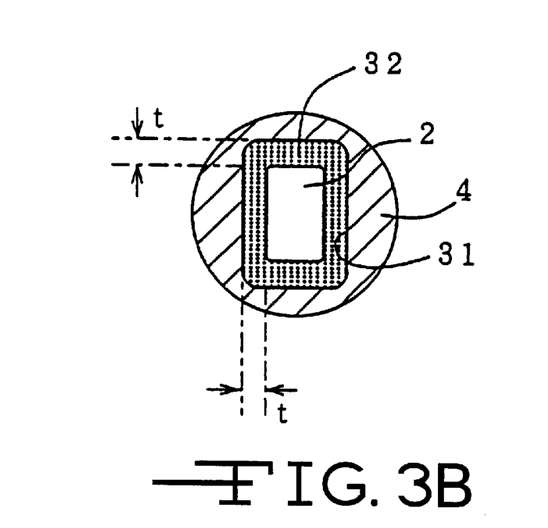
FIG. 3(b) is a full, sectional view of a main portion of the oxygen sensor of FIG. 1 taken along line A—A of FIG. 3(a)
Figure 3C:
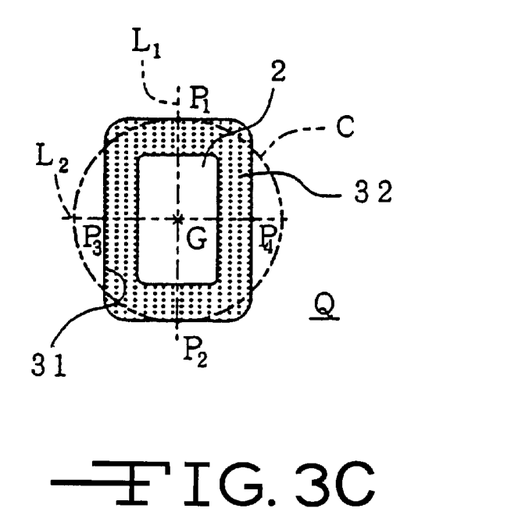
FIG. 3(c) is an enlarged, sectional, explanatory view of a main portion of the oxygen sensor of FIG. 1.

In accordance with a second aspect of the present invention, the gas sensor has the following features (see FIGS. 3(a) and 3(c) for the following description). That is, the sensor element (2) has a rectangular cross section along a plane Q perpendicular to the axis of the sensor element (2). On the plane Q, a line L1 is drawn such that the line L1 passes through the centroid G of the cross section of the sensor element (2) and perpendicularly intersects the shorter sides of the cross section of the sensor element (2). The intersections between the line L1 and the inner surface defining the cavity (31) are taken as P1 and P2, respectively. Similarly, a line L2 is drawn such that the line L2 passes through the centroid G of the cross section of the sensor element (2) and perpendicularly intersects the longer sides of the cross section of the sensor element (2). The intersections between the line L2 and the inner surface defining the cavity (31) are taken as P3 and P4, respectively. Further, while the longer of the distances GP1 and GP2 (or either one when GP1=GP2) is used as a radius, a circle C centered at the centroid G is drawn. The sectional profile of the inner surface defining the cavity (31) is determined such that both the points P3 and P4 fall within the circle C.

When the sensor element has a rectangular cross section and, as shown in FIG. 14, the cavity defining inner surface—i.e., the outer circumference of the sealing material layer charged in the cavity—has a circular profile, thick wall portions are formed in regions along the longer sides of the cross section of the sensor element, which causes stress concentration at thin wall portions formed along the shorter sides of the cross section. In order to solve this problem, in accordance with the second aspect of the present invention, the sectional profile of the cavity defining inner surface of the insulator (or the sectional outer profile of the sealing material layer) is set such that both the points P3 and P4 fall within the circle C. In this case, since the sealing material layer has a reduced wall thickness in regions along the longer sides of the cross section of the sensor element, the above-described problem can be avoided.

Preferably, the average wall thickness of the sealing material layer formed around the sensor element is adjusted within the range of 0.2 to 5 mm. When the thickness of the sealing material layer becomes less than 0.2 mm, the air tightness between the sensor element and the insulator is impaired. Further, since the size and weight of gas sensors mounted on automobiles and like have recently been reduced drastically, it has became difficult to secure space for allowing use of a sealing material layer having a thickness of 5 mm or greater. Further, when the thickness of the sealing material layer exceeds 5 mm, the absolute amount of thermal contraction of the sealing material layer increases, thereby increasing the thermal stress acting on the sensor element disposed inside the sealing material layer, possibly shortening the life of the sensor element. More preferably, the average wall thickness of the sealing material layer is adjusted within the range of 0.3 to 3 mm.

Further, when the sensor element has a rectangular cross section, the maximum thickness of the sealing material layer in regions along the shorter sides is preferably set substantially equal to the maximum thickness of the sealing material layer in regions along the longer sides. Specifically, the cavity defining inner surface preferably has a rectangular sectional profile such that the centroid of the sectional profile of the cavity defining inner surface substantially coincides with the centroid of the cross section of the sensor element and such that the sectional profile of the cavity defining inner surface corresponds to that of the cross section of the sensor element. In this case, each of the four corners of the sectional profile of the cavity defining inner surface preferably has a rounded or chamfered shape. Alternatively, the cavity defining inner surface has an elliptical sectional profile such that the centroid of the sectional profile of the cavity defining inner surface substantially coincides with the centroid of the cross section of the sensor element and such that the major axis of the ellipse extends along the longitudinal direction of the cross section of the sensor element.

The gas sensor of the present invention may have the following structure. That is, the gas sensor comprises an outer cylinder, a metallic shell, a sensor element, a sealing-material layer, and a cushion layer. The metallic shell is disposed inside the outer cylinder. The sensor element is disposed inside the metallic shell and is adapted to detect a component of a measurement gas. The sealing material layer is mainly made of glass and is disposed between the outer surface of the sensor element and the inner surface of the metallic shell or between the outer surface of the sensor element and the inner surface of an insulator disposed between the metallic shell and the sensor element. The cushion layer is made of a porous inorganic substance and is disposed on at least one side of the sealing material layer with respect to the axial direction of the sensor element.

In the above gas sensor of the present invention, the cushion layer made of a porous inorganic substance is disposed on at least one side of the sealing material layer with respect to the axial direction of the sensor element. The thus disposed cushion layer eases stress concentration in a boundary region between a portion of the sensor element covered with the sealing material layer and an uncovered portion, thereby extending sensor element life. In this case, the cushion layer conceivably produces the following effects.

(1) When a mechanically or thermally induced impact force acts on the sensor element, the cushion layer supports the portion of the sensor element not covered with the sealing material layer to thereby suppress a displacement of the portion which would otherwise occur in a direction perpendicular to the axis of the sensor element, thereby suppressing a strong local bending stress which would otherwise occur in the sensor element.

(2) During heating/cooling in a step of sealing with glass, the cushion layer alleviates a radial compressive force or a bending stress which would otherwise be imposed on the sensor element due to a contraction differential between glass (material of the sealing-material layer) and the sensor element or the metallic shell or the insulator.

The cushion layer may be disposed to be in contact with the sealing material layer or a predetermined gap or another layer may be disposed between the cushion layer and the sealing material layer.

The cushion layers may be disposed on opposite sides of the sealing material layer with respect to the axial direction of the sensor element. This arrangement alleviates stress concentration which would otherwise occur in the sensor element on opposite sides of the sealing material layer, thereby further improving the durability of the sensor element. In this case, the cushion layers provided on opposite sides of the sealing material layer may be of different materials or of the same material.

The sensor element may have an elongated shape with a sensing portion formed at a tip section thereof and may be inserted through the metallic shell such that the sensing portion projects therefrom. In this case, the cushion layer which is in contact with the end of the sealing material layer located closer to the tip section of the sensor element contains filler particles and binder particles. The filler particles are superior in heat resistance to glass contained in the sealing material layer. The binder particles partially fill gaps among filler particles, are superior in heat resistance to glass contained in the sealing material layer, and are lower in softening temperature than the filler particles.

Specifically, the cushion layer located on the near side of the sealing material layer as viewed from the tip section of the sensor element is more susceptible to high temperature than is the sealing material layer. Therefore, in the cushion layer, the filler particles, which are superior in heat resistance to glass contained in the sealing material layer, are bonded by the binder particles, which are lower in softening temperature than the filler particles, but are superior in heat resistance to glass contained in the sealing material layer. Accordingly, sufficient heat resistance as well as stress alleviating properties can be imparted to the cushion layer, which is exposed to an environment more severe than that to which the sealing material layer is exposed. In this case, the filler particles may be mainly formed of $Al_2O_3$ or talc, and are preferably of $Al_2O_3$ in view of its excellent heat transmission and heat resistance. The binder particles are preferably of clay, for example, since clay particles can fuse together at a temperature of forming the sealing material layer (a sealing temperature).

In the configuration that the sensor element is inserted through the metallic shell such that the sensing portion projects therefrom and that the cushion layer is disposed in contact with the end of the sealing material layer located closer to the sensing portion, the cushion layer is preferably formed such that its diameter decreases toward the sensing portion. The cushion layer may be formed in the following manner. The sensor element is inserted through a cavity formed in the metallic shell or the insulator. Then, the cavity is filled with powder material for the cushion layer (or powder compact). The thus formed preliminary assembly is heated to a sealing temperature. In this case, since the cushion layer (in other words, the cavity formed in the metallic shell or the insulator) assumes the above-mentioned shape, the filling density of the material powder at a smaller diameter portion of the cavity can be increased when the material powder is filled into the cavity, and thus improving the sealing of the sensor element against the cushion layer.

DESCRIPTION OF THE PREFERRED EMBODIMENTS

Figure 1:
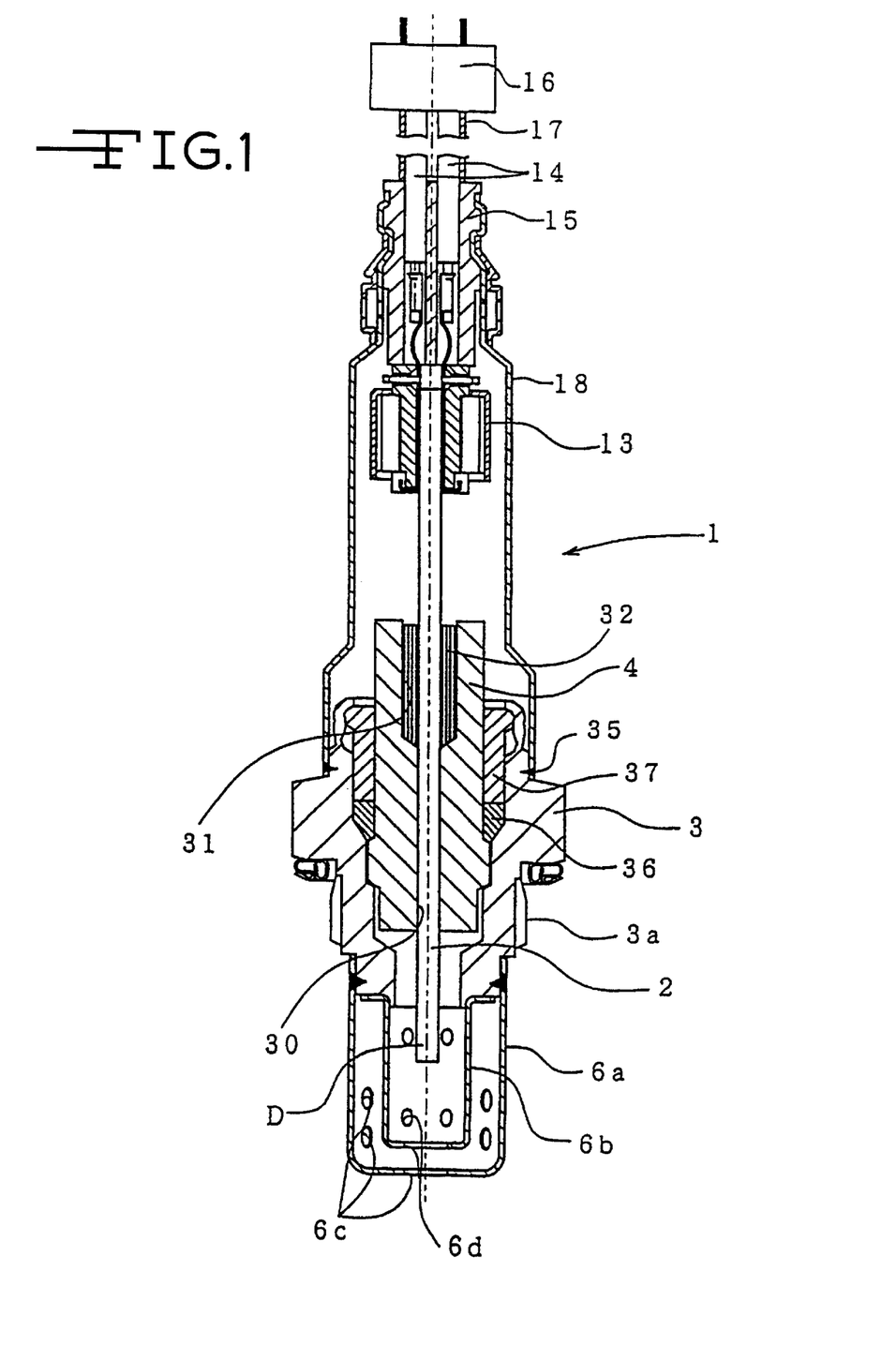
FIG. 1 is a longitudinal, sectional view of a gas sensor such as an oxygen sensor of a first embodiment of the present invention.

FIG. 1 shows an embodiment of a gas sensor of the present invention. An oxygen sensor 1 is adapted to detect the concentration of oxygen contained in an exhaust gas emitted from an automobile or a like apparatus. The oxygen sensor 1 is commonly referred to as a λ sensor or an $O_2$ sensor and includes an elongated ceramic element 2 (sensor element). The tip of the ceramic element 2 is exposed to high-temperature exhaust gas flowing through an exhaust pipe.

Figure 2A:
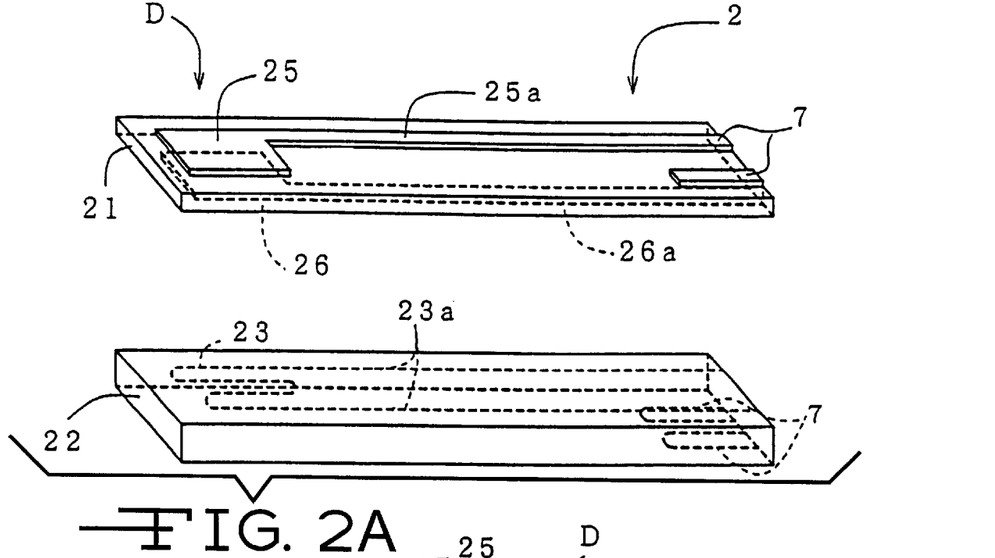
FIG. 2(a) is a perspective view showing the components of a ceramic sensor element of the gas sensor of FIG. 1 in preassembly configuration.

The ceramic element 2 is in the form of an elongated sheet having a rectangular cross section. As shown in FIG. 2(a), the ceramic element 2 is a laminate of an oxygen concentration cell element 21 and a heater 22. The oxygen concentration cell element 21 has the form of an elongated sheet. The heater 22 also has the form of an elongated sheet and is adapted to heat the oxygen concentration cell element 21 to a predetermined activation temperature. The oxygen concentration cell element 21 is made of an oxygen-ion conductive solid electrolyte. A typical example of such a solid electrolyte is $ZrO_2$ obtained through solid solution of $Y_2O_3$ or CaO. Alternatively, there may be used a solid solution of $ZrO_2$ and an oxide of an alkali earth metal or rare earth metal. $ZrO_2$ serving as a base may contain $HfO_2$. The heater 22 is a known ceramic heater composed of a ceramic substrate and a resistance heating pattern 23. The resistance heating pattern 23 is made of a high melting point metal or an electrically conductive ceramic and is embedded in the ceramic substrate.

In the oxygen concentration cell element 21, porous electrodes 25 and 26 capable of dissociating oxygen molecules are formed on opposite surfaces at a longitudinal end portion (a portion projecting from the tip of a metallic shell 3). The electrodes 25 and 26 and a portion of the solid electrolyte interposed therebetween constitute a sensing portion D.

Electrode leads 25a and 26a are integrated with the porous electrodes 25 and 26, respectively, and extend toward the mounting end of the oxygen sensor 1 along the longitudinal direction of the oxygen concentration cell element 21. An end of the electrode lead 25a extending from the electrode 25, which end does not face the heater 22, is used as an electrode terminal 7. As shown in FIG. 2(c), the electrode lead 26a extending from the electrode 26, which lead faces the heater 22, is connected to an electrode terminal 7 formed on the opposite side of the oxygen concentration cell element 21, by means of a via hole 26b formed in the oxygen concentration cell element 21 in its thickness direction. In other words, in the oxygen concentration cell element 21, the electrode terminals 7 for the porous electrodes 25 and 26 are formed in parallel on the same surface and at an end portion of the surface. The electrodes, terminals, and via hole are formed by the steps of: screen printing respective patterns through use of a paste of metal powder having catalytic activity for oxygen molecule dissociation reaction, such as a paste of Pt or Pt alloy; and firing the printed patterns.

Figure 2B:
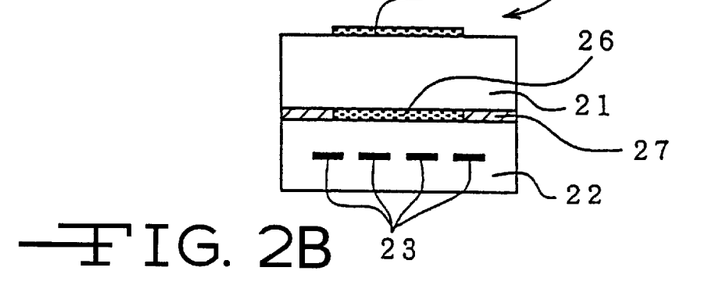
FIG. 2(b) is an enlarged, transverse sectional view of the assembled components of a ceramic sensor element of the gas sensor of FIG. 1.
Figure 2C:
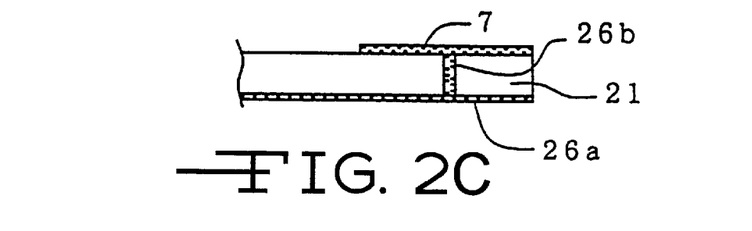
FIG. 2(c) is an enlarged, fragmentary, sectional view of an oxygen concentration cell element of the sensor element of the gas sensor of FIG. 1.
Figure 2D:
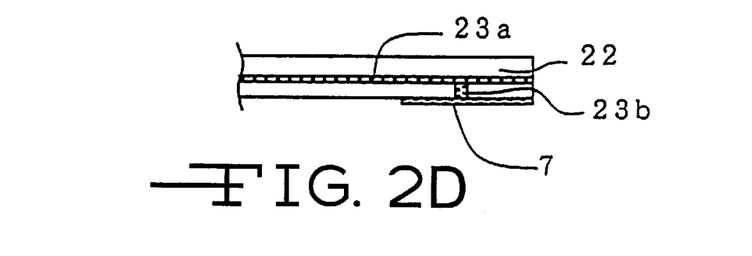
FIG. 2(d) is an enlarged, fragmentary, sectional view of a heater of a sensor element of the gas sensor of FIG. 1.

As shown in FIG. 2(d), in the heater 22, leads 23a for supplying power to the resistance heating pattern 23 are connected, by means of respective via holes 23b, to electrode terminals 7 formed at one end of a surface of the heater 22 which does not face the oxygen concentration cell element 21.

As shown in FIG. 2(b), the oxygen concentration cell element 21 and the heater 22 are bonded together via a ceramic layer 27. The ceramic layer 27 is made of a $ZrO_2$ ceramic or an $Al_2O_3$ ceramic. The electrode lead 26a (porous) is bonded to the porous electrode 26 on the ceramic layer 27 side. A weak pumping current is applied between the porous electrode 26 and the opposed porous electrode 25 such that oxygen is pumped into the porous electrode 26. The thus-pumped-in oxygen is discharged to the atmosphere via the electrode lead 26a. As a result, the concentration of oxygen contained in the porous electrode 26 is held slightly higher than that of the atmosphere; thus, the porous electrode 26 functions as an oxygen reference electrode. The porous electrode 25 opposite the porous electrode 26 serves as a sensing electrode which comes into contact with exhaust gas.

The ceramic element 2 having the above structure is inserted through a through-hole 30 formed in an insulator 4. The insulator 4 is disposed inside the metallic shell 3, which is fixed on an exhaust pipe. The ceramic element 2 is fixed in the insulator 4 such that the sensing portion D located at a tip portion thereof projects from the tip of the metallic shell 3. A cavity 31 having a diameter larger than that of the through-hole 30 is formed in the insulator 4 such that the cavity 31 and the through-hole 30 are arranged in series in the axial direction of the ceramic element 2. One end of the cavity 31 communicates with the rear end of the through-hole 30, whereas the other end opens at the rear end surface of the insulator 4. A space which is defined by the outer surface of the ceramic element 2 and the inner surface of the insulator 4 which defines the cavity 31 is filled with a sealing material layer 32, for the purpose of attaining sealing. The sealing material layer 32 is mainly made of glass (for example, crystallized zinc silica boric acid glass having a softening temperature of 660° C.).

As shown in FIG. 3(b), the ceramic element 2 has a sectional profile of a generally rectangular shape. Meanwhile, the sectional profile of the inner surface of the insulator 4 defining the cavity 31; i.e., the sectional outer profile of the sealing material layer 32, has a rectangular shape so as to correspond to the sectional profile of the ceramic sensor 2. Further, the four corners of the sectional profile of the inner surface of the insulator 4 defining the cavity 31 or the sectional outer profile of the sealing material layer 32 have a round (or chamfered) shape in order to mitigate stress concentration. The size of the round (or chamfered) shape is preferably adjusted within the range of 0.3 to 3 mm. Further, the centroid of the cross section of the ceramic element 2 substantially coincides with that of the sectional profile of the inner surface of the insulator 4 defining the cavity 31.

The sectional profile of the sealing material layer 32 or the cavity 31 can be expressed from a different viewpoint, as follows. That is, as shown in FIG. 3(c), on the plane Q perpendicular to the axis of the ceramic element 2 (FIG. 3(a)), a line L1 is drawn such that the line L1 passes through the centroid G of the cross section of the ceramic element 2 and perpendicularly intersects the shorter sides of the cross section of the ceramic element 2. The intersections between the line L1 and the inner surface defining the cavity 31 are taken as P1 and P2, respectively. Similarly, a line L2 is drawn such that the line L2 passes through the centroid G of the cross section of the ceramic element 2 and perpendicularly intersects the longer sides of the cross section of the ceramic element 2. The intersections between the line L2 and the inner surface defining the cavity 31 are taken as P3 and P4, respectively. Further, while the longer of the distances GP1 and GP2 (or either one when GP1=GP2) is used as a radius, a circle C centered on the centroid G is drawn. The sectional profile of the inner surface defining the cavity 31 is determined such that both the points P3 and P4 fall within the circle C.

Further as shown in FIG. 3(b), the thickness t of the sealing material layer 32 formed around the ceramic element is adjusted within the range of 0.2 to 5 mm, preferably, within the range of 0.3 to 3 mm. Moreover, the thickness t of the sealing material layer 32 in regions along the shorter sides of the cross section of the ceramic element 2 is preferably set substantially equal to that of the sealing material layer in regions along the longer sides.

Next, as shown in FIG. 1, a talc ring 36 and a caulking ring 37 are fitted between the insulator 4 and the metallic shell 3 such that they are located adjacent to each other in the axial direction. The rear end portion of the metallic shell 3 is caulked such that the rear end portion is bent and pressed toward the insulator 4 via the caulking ring 37, to thereby fix the insulator 4 and the metallic shell 3. Double protection covers 6a and 6b of metal are fixedly attached to the tip portion of the metallic shell 3 through laser welding or resistance welding (for example, spot welding) in such a manner as to cover a projected portion of the ceramic element 2. The covers 6a and 6b each have a cap shape and have holes 6c and 6d, respectively, formed therein for introducing into a cover 6 a high-temperature exhaust gas flowing through an exhaust pipe. The rear end portion of the metallic shell 3 is fitted into the tip end portion of an outer cylinder 18. At the overlap of the metallic shell 3 and the outer cylinder 18, the metallic shell 3 and the outer cylinder 18 are connected in an airtight manner by means of an annular weld zone (for example, a laser weld zone) 35. At the overlap, the metallic shell 3 and the outer cylinder 18 may be connected through circumferential caulking instead of by laser welding. However, when a particularly high degree of watertightness is desired, laser welding is preferred because of its excellent liquid tightness.

As shown in FIG. 1, lead wires 14 are electrically connected to the electrode terminals 7 (four; see FIG. 2) of the ceramic element 2 via a connector 13. A total of four lead wires 14 extend to the exterior of the oxygen sensor 1 through a grommet 15 and are connected to a connector plug 16. Portions of the lead wires 14 extending between the connector plug 16 and the oxygen sensor 1 are collectively covered with a protection tube 17.

The operation of the oxygen sensor 1 will next be described.

As shown in FIG. 1, the oxygen sensor 1 is fixedly attached to an automobile exhaust pipe by means of a threaded portion 3a of the metallic shell 3. The connector plug 16 is connected to a controller (not illustrated). When the sensing portion D is exposed to exhaust gas, the porous electrode 25 (FIG. 2) of the oxygen concentration cell element 21 comes into contact with the exhaust gas. As a result, an electromotive force is generated by the concentration cell effect, which is induced in the oxygen concentration cell element 21 according to the concentration of oxygen contained in the exhaust gas. The generated electromotive force is outputted as a sensor output via the electrode leads 25a and 26a, the electrode terminals 7, and the lead wires 14. A λ sensor (or $O_2$ sensor) of this kind shows a characteristic that an electromotive force generated by the concentration cell effect varies abruptly in the vicinity of a region where an exhaust gas composition shows a theoretical air-fuel ratio, and is thus used widely for detection of an air-fuel ratio.

The oxygen sensor 1 is often attached to an exhaust manifold or an exhaust pipe located near a suspension system and tires. In this case, the sensor may be exposed to high temperature and subjected to a strong thermal shock caused by splashing of water. In the case shown in FIG. 14, in which the inner surface of the insulator 104 defining the cavity 131 has a circular sectional profile, stresses concentrate at the thin wall portions of the sealing material layer 132 formed along the shorter sides of the cross section of the sensor element 102. By contrast, in the structure of the present invention shown in FIG. 3(b), the thickness of the sealing material layer 32 in regions along the longer sides of the cross section of the ceramic element 2 can be reduced, so that the above-described problem can be avoided.

Figure 4:
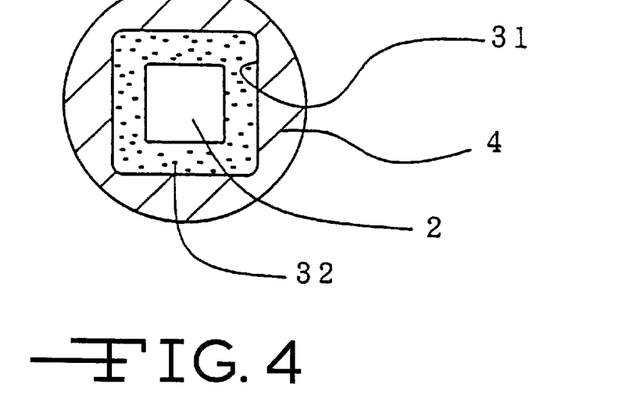
FIG. 4 is a transverse, sectional view showing a modification of the oxygen sensor of FIG. 1.
Figure 5A:
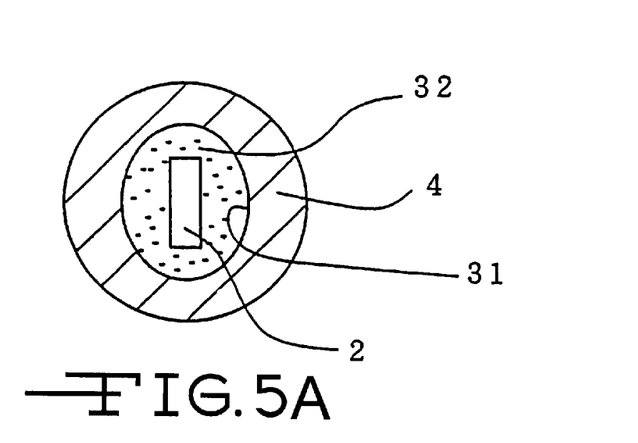
FIG. 5(a) is a transverse, sectional view of the oxygen sensor of FIG. 1 showing a first modification.
Figure 5B:
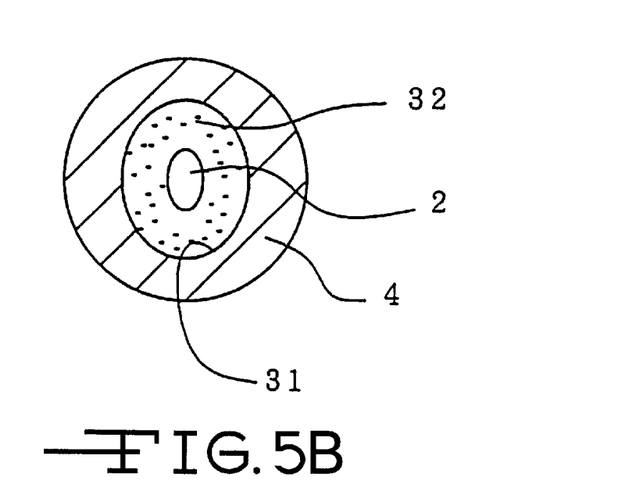
FIG. 5(b) is a transverse, sectional view of the oxygen sensor of FIG. 1 showing a second modification.

When the ceramic element 2 has a square cross section as shown in FIG. 4, the inner surface defining the cavity 31 (i.e., the outer circumferential surface of the sealing material layer 32) has a square sectional profile in order to correspond to the cross section of the ceramic element 2. When the ceramic element 2 has a rectangular cross section as shown in FIG. 5(*a*), the inner surface defining the cavity 31 (i.e., the outer circumferential surface of the sealing material layer 32) may have an elliptical sectional profile such that the centroid of the sectional profile of the cavity-defining inner surface substantially coincides with the centroid of the rectangular cross section of the ceramic element 2 and such that the major axis of the ellipse extends along the longitudinal direction of the cross section of the ceramic element 2. Further, when the ceramic element 2 has an elliptical cross section as shown in FIG. 5(*b*), the inner surface defining the cavity 31 (i.e., the outer circumferential surface of the sealing material layer 32) may have an elliptical sectional profile similar to that of the cross section of the sensor element.

Figure 6:
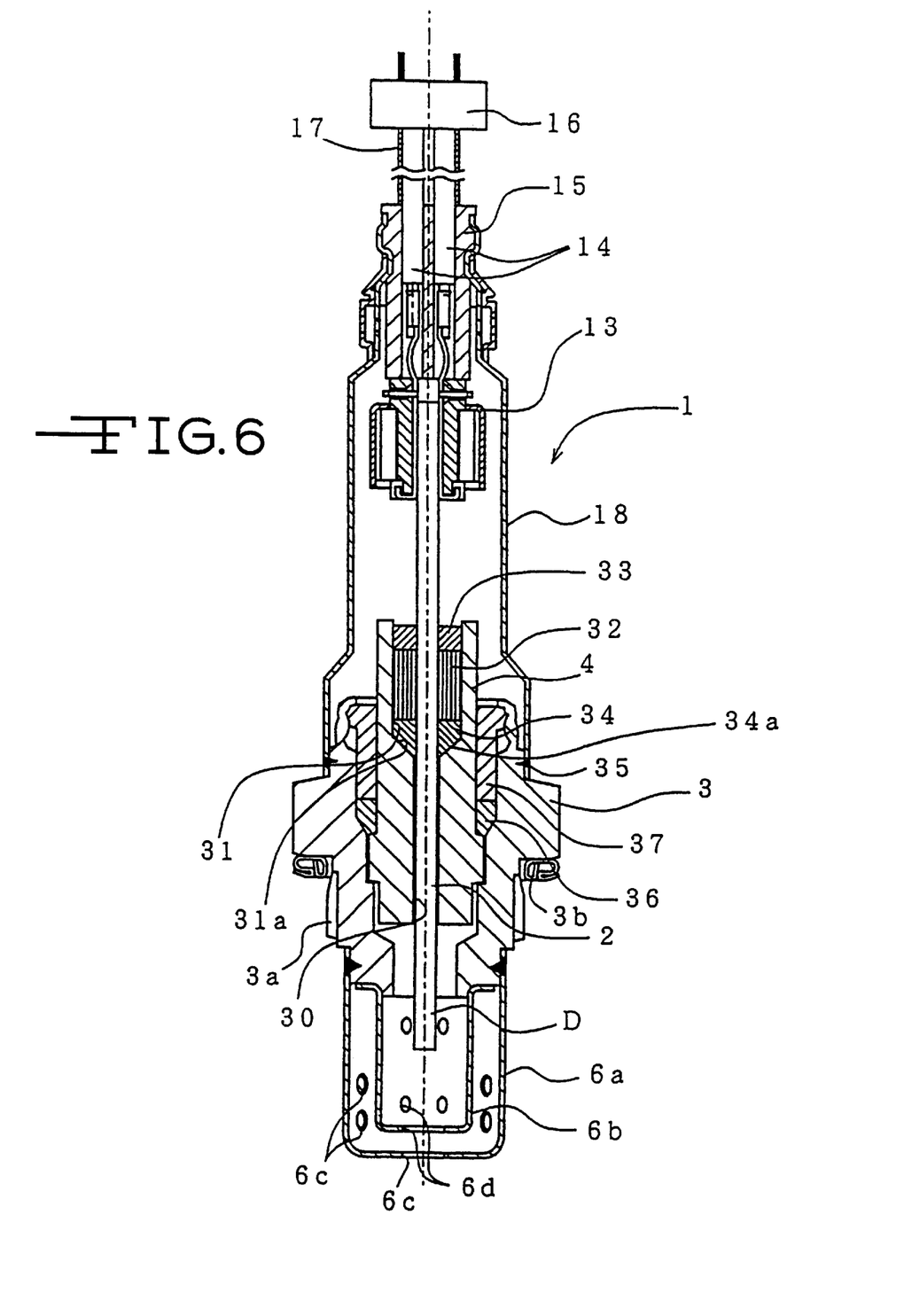
FIG. 6 is a longitudinal, sectional view showing a modification of the oxygen sensor of FIG. 1 in which cushion layers are provided adjacent to the sealing material layer.
Figure 7:
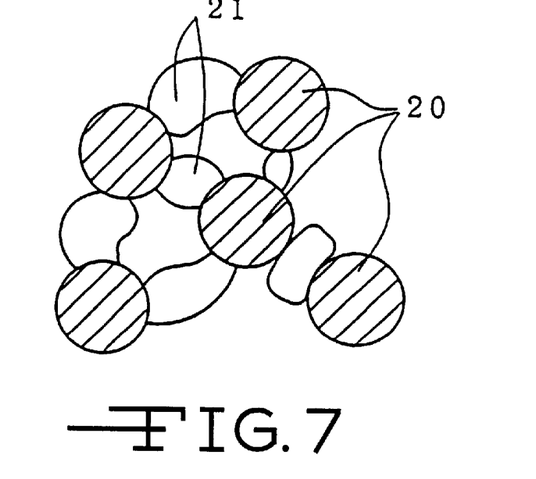
FIG. 7 is a schematic view illustrating the structure of a cushion layer.

As shown in FIG. 6, cushion layers 33 and 34 are formed on opposite sides of the sealing material layer 32 as viewed along the axial direction of the ceramic element 2, in such a manner as to fill the space defined by the outer surface of the ceramic element 2 and the inner surface of the insulator 4 defining the cavity 31. As shown in FIG. 7, the cushion layers 33 and 34 are made of a porous inorganic substance. The porous inorganic substance includes filler particles 20 and binder particles 21. The filler particles 20 are superior in heat resistance to glass contained in the sealing material layer 32. The binder particles 21 partially fill gaps among the filler particles 20 and have a softening temperature lower than that of the filler particles 20. The cushion layer 34 is in contact with the front end of the sealing material layer 32; i.e., the end located closer to the tip section of the ceramic element 2. The cushion layer 34 is composed of $Al_2O_3$ particles serving as the filler particles 20 and inorganic substance particles—for example, clay particles—serving as the binder particles 21. The clay particles are superior in heat resistance to glass contained in the sealing material layer 32 and have a softening temperature lower than that of the filler particles 20. The clay particles may be mainly composed of hydrous alumino-silicate. For example, the clay particles may be mainly composed of two or more clay minerals (or their composite substances) selected from the group consisting of allophane, imogolite, hisingerite, smectites, kaolinite, halloysite, montmorillonite, illite, and vermiculite. From the point of view of oxide components, the clay particles may contain $SiO_2$ and $Al_2O_3$ and, as needed, may further contain, singly or in combination, $Fe_2O_3$, $TiO_2$, CaO, MgO, $Na_2O$, and $K_2O$.

As shown in FIG. 6, the tip end of the cavity 31 tapers down toward the tip of the ceramic element 2, thereby forming a reduced diameter portion 31*a*. Similarly, the outer surface of the tip end of the cushion layer 34 tapers down with the reduced diameter portion 31*a*, thereby forming a reduced diameter portion 34*a*.

The cushion layer 33 is in contact with the rear end of the sealing material layer 32. The filler particles 20 (FIG. 7) contained in the cushion layer 33 are talc particles. The binder particles 21 (FIG. 7) contained in the cushion layer 33 are particles having a softening temperature slightly higher than that of glass contained in the sealing material layer 32; for example, crystallized glass particles (crystallized zinc silica boric-acid glass; softening temperature 680° C.).

Figures 9A, 9B:
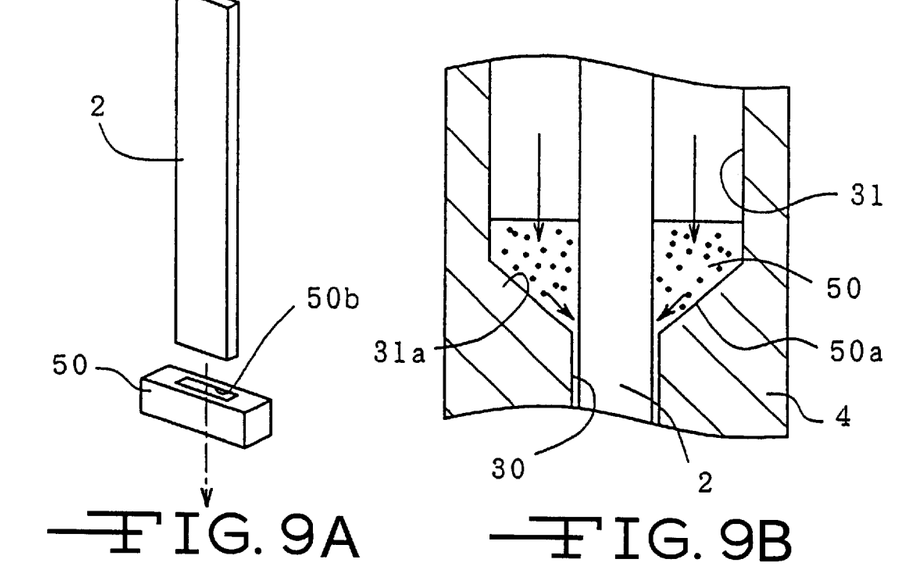
FIGS. 9(a), 9(b), 9(c) and 9(d) are diagrammatic views illustrating the initial steps of a process for manufacturing the oxygen sensor of FIG. 6.
Figure 9C:
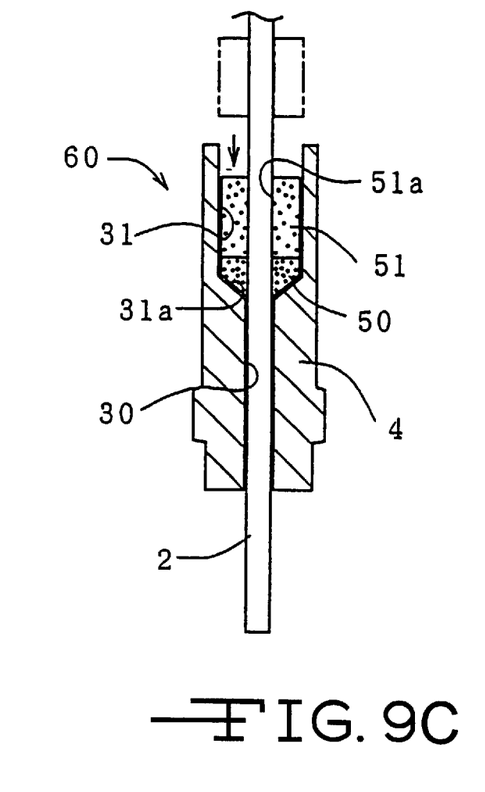
Figure 9D:
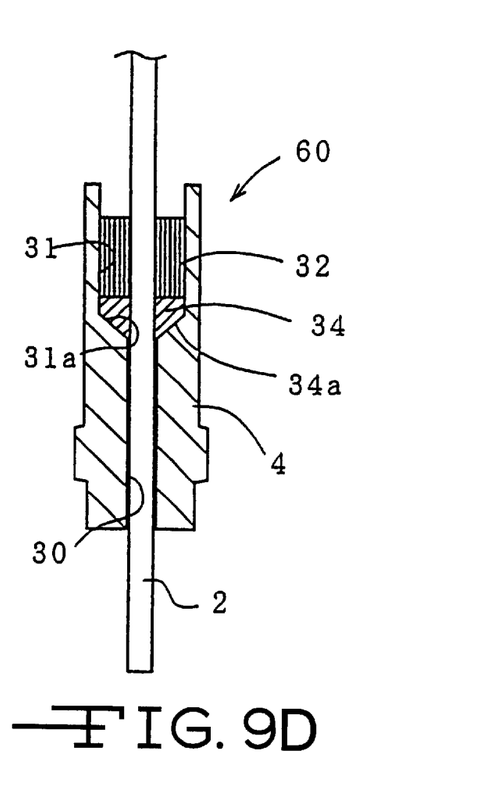

As shown in FIGS. 9(*a*), 9(*b*), 9(*c*), 9(*d*), 10(*a*) and 10(*b*), the above-described sealing structure of the ceramic element 2 and the insulator 4 is manufactured in the following manner, for example. First, a material powder compact for forming the cushion layer 34 is manufactured. In the present embodiment, $Al_2O_3$ powder serving as the filler particles 20 and clay powder serving as the binder particles 21 are mixed. The resultant mixture is pressed into a powder compact 50 shown in FIG. 9(*a*). The powder compact 50 has a through-hole 50*b* formed in the central portion thereof and extending in the axial direction thereof.

Next, the ceramic element 2 is inserted through the through-hole 50*b* formed in the powder compact 50. Then, the ceramic element 2 is inserted from its tip through the through-hole 30 formed in the insulator 4. The powder compact 50 is placed in the cavity 31 formed in the insulator 4 and is lightly pressed against the insulator 4 in the axial direction of the ceramic element 2. In this case, as shown in FIG. 9(*b*), the tapered surface 50*a* of the powder compact 50 is pressed against and brought into close contact with the reduced diameter portion 31*a* of the cavity 31. Accordingly, the tapered portion of the powder compact 50 is subjected to a radial reaction effected by the reduced diameter portion 31*a* and is thus further compacted. Next, as shown in FIG. 9(*c*), an inorganic material powder which is mainly composed of glass is formed into a cylindrical shape, yielding a powder compact 51. The powder compact 51 is fitted onto the ceramic element 2 from the rear end thereof in such a manner that the ceramic element 2 is inserted through a through-hole 51*a* formed in the powder compact 51. Thus, the powder compact 51 is placed in the cavity 31 adjacent to the powder compact 50, thereby forming an insulator-sensor-element assembly 60. This arrangement provides improved sealing between the ceramic element 2 and the wall surface of the through-hole 30 of the insulator 4.

The insulator-sensor-element assembly 60 is heated to a temperature of 800° C. to 1000° C. As a result, the powder compact 51 becomes the sealing material layer 32 through fusion of the inorganic material powder which is mainly composed of glass, thereby sealing the joint between the ceramic element 2 and the insulator 4. Through fusion of the clay powder while $Al_2O_3$ particles are dispersed, the powder compact 50 becomes the cushion layer 34 as shown in FIG. 9(*d*).

Figure 10A:
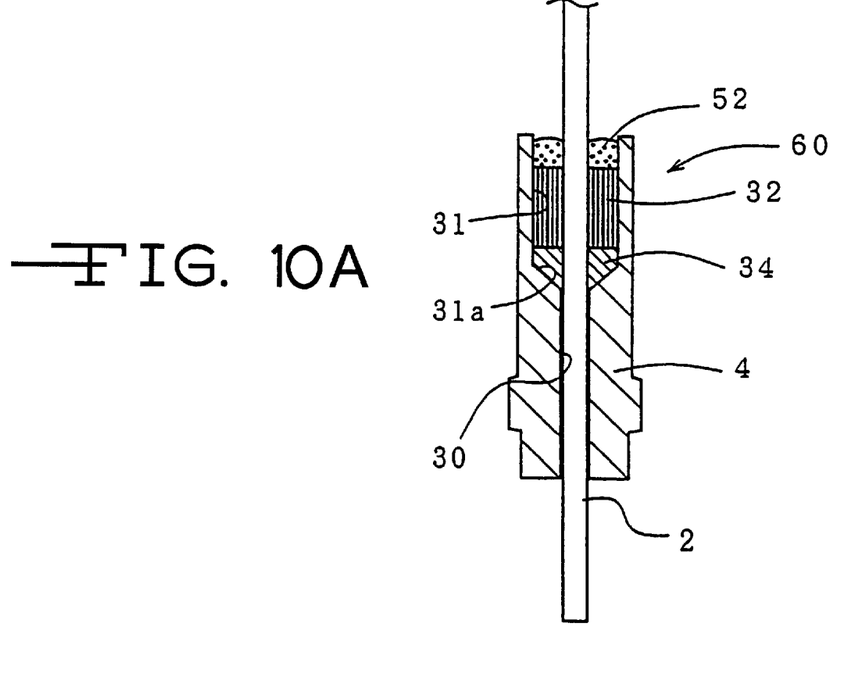
FIGS. 10(a) and 10(b) are diagrammatic views illustrating the final steps of a process for manufacturing the oxygen sensor of FIG. 6 continued from FIG. 9.
Figure 10B:
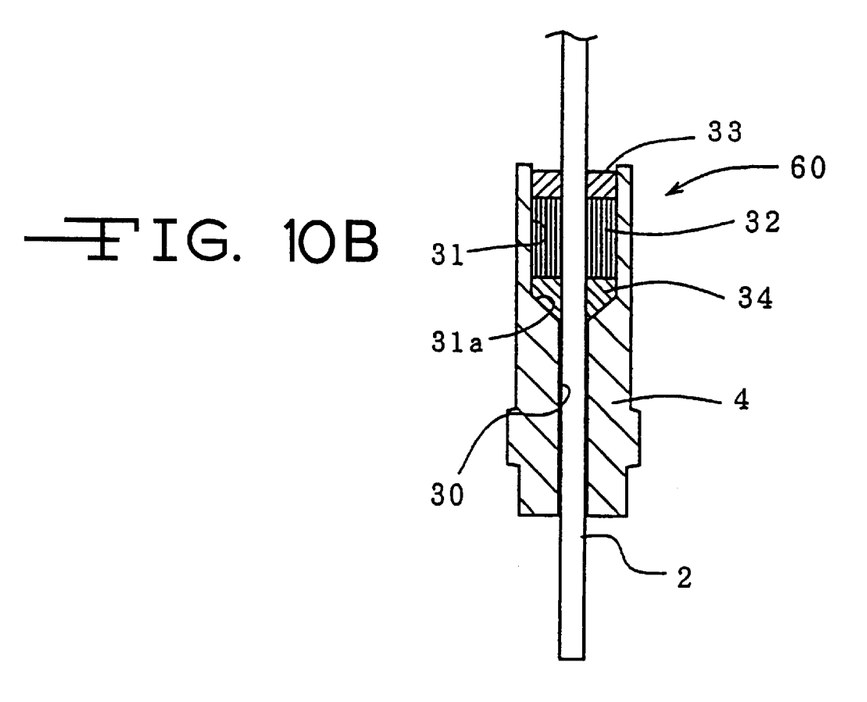

Next, as shown in FIG. 10(*a*), a material powder 52 (in the present embodiment, a mixed powder of talc and crystallized glass) for the cushion layer 33 is charged into a space between the ceramic element 2 and the insulator 4 at a rear portion of the cavity 31. The charged material powder 52 is lightly pressed. Subsequently, the insulator-sensor-element assembly 60 is again heated to a temperature of 700° C. to 1000° C. (preferably 700° C. to 900° C.) As a result, through fusion of the crystallized glass powder, the charged material powder 52 becomes the cushion layer 33 as shown in FIG. 10(*b*). In place of directly charging the material powder 52 into the cavity 31, the material powder 52 may be pressed into a compact, which is then placed in the cavity 31.

Figure 8A:
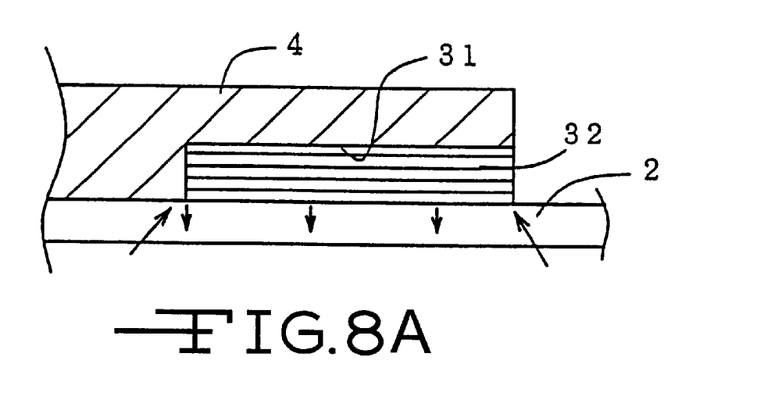
FIG. 8(a) is a diagrammatic view of a conventional oxygen sensor.

As described above, the oxygen sensor 1 is often attached to an exhaust manifold or an exhaust pipe located near a suspension system and tires. In this case, a flipped stone may hit the sensor, or the sensor may be subjected to a strong thermal shock caused by splashing of water during exposure to high temperature. According to the configuration of a conventional oxygen sensor, as shown in FIG. 8(*a*), the cavity 31 formed in the insulator 4 is merely filled with the sealing material layer 32 which is mainly composed of glass. For example, when a bending stress is applied to the ceramic element 2 due to a shock caused by a flipped stone or to thermal shock, stress concentration tends to arise in a boundary region between a portion of the ceramic element 2 covered with the sealing material layer 32 and an uncovered portion in the axial direction of the ceramic element 2, potentially shortening the life of the ceramic element 2.

Figure 8B:
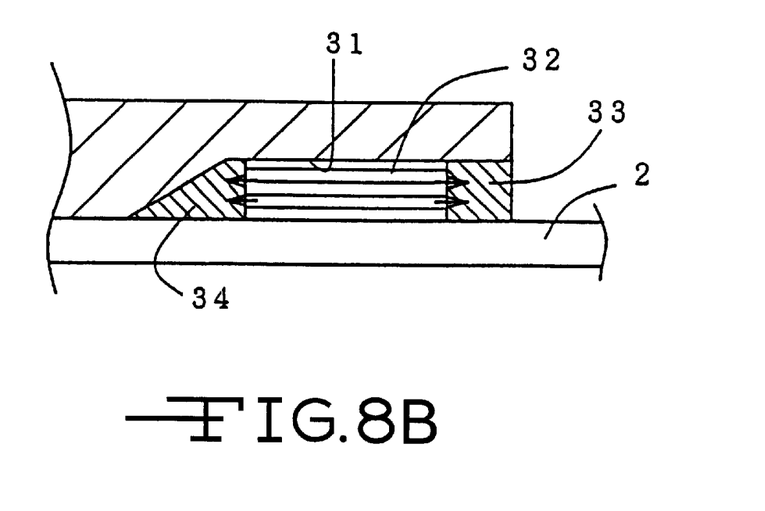
FIG. 8(b) is a diagrammatic view of an oxygen sensor of the present invention.

By contrast, according to the above-described configuration of the oxygen sensor 1 of the present invention, as shown in FIG. 8(b), the cushion layers 33 and 34 made of a porous inorganic substance are disposed on opposite sides of the sealing material layer 32 with respect to the axial direction of the ceramic element 2. Accordingly, even when the force of a mechanical or thermal shock acts on the ceramic element 2, stress concentration is less likely to arise in the above-mentioned boundary region, thereby prolonging the life of the ceramic element 2. Conceivably, while supporting portions of the ceramic element 2 which are not covered with the sealing material layer 32, the cushion layers 33 and 34 are deformed in a direction perpendicular to the axial direction of the ceramic element 2, thereby preventing a strong bending stress from acting on the above-mentioned boundary region. Also, conceivably, in heating/cooling operation of a glass sealing step, the cushion layers 33 and 34 alleviate a radial compressive force or a bending stress which would otherwise act on the ceramic element 2 due to a contraction differential among glass components which constitute the sealing material layer 32, the ceramic element 2, and the metallic shell 3 or the insulator 4. Thus, the employment of the cushion layers 33 and 34 improves the endurance of the ceramic element 2 during the step of sealing with glass, thereby improving the yield of manufacture of sensors.

Figure 11A:
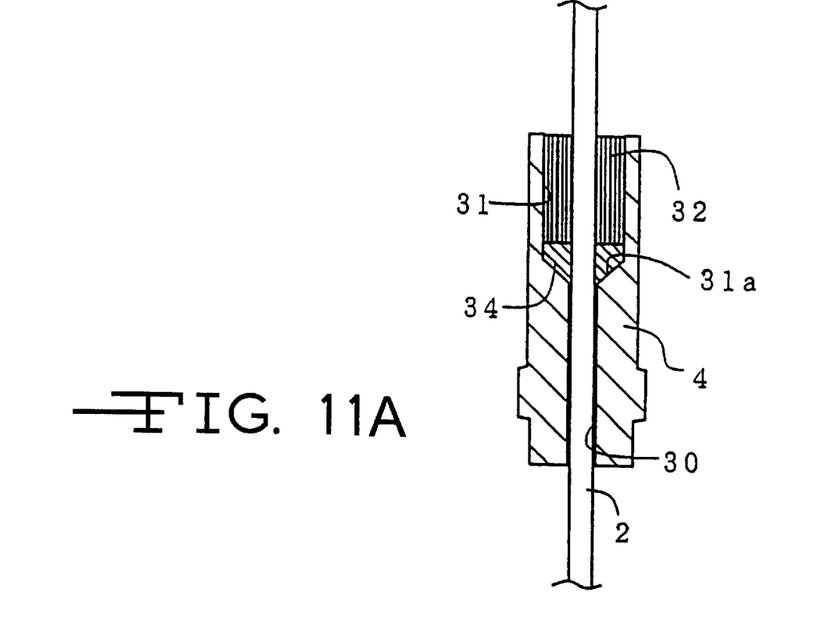
FIG. 11(a) is a full, sectional view showing a first modification of the cushion layer of the oxygen sensor FIG. 6.

Since a tip portion of the ceramic element 2 is disposed in a high-temperature exhaust pipe, the near side of the sealing material layer 32 as viewed from the tip of the ceramic element 2 is susceptible to the influence of heat. By contrast, in a certain environment of application, the far side of the sealing material layer 32 is less susceptible to the influence of heat because of a relatively long distance from a heat source. In this case, as shown in FIG. 11(a), the cushion layer 33, which is located on the far side of the insulator 4, may be omitted.

Figure 11B:
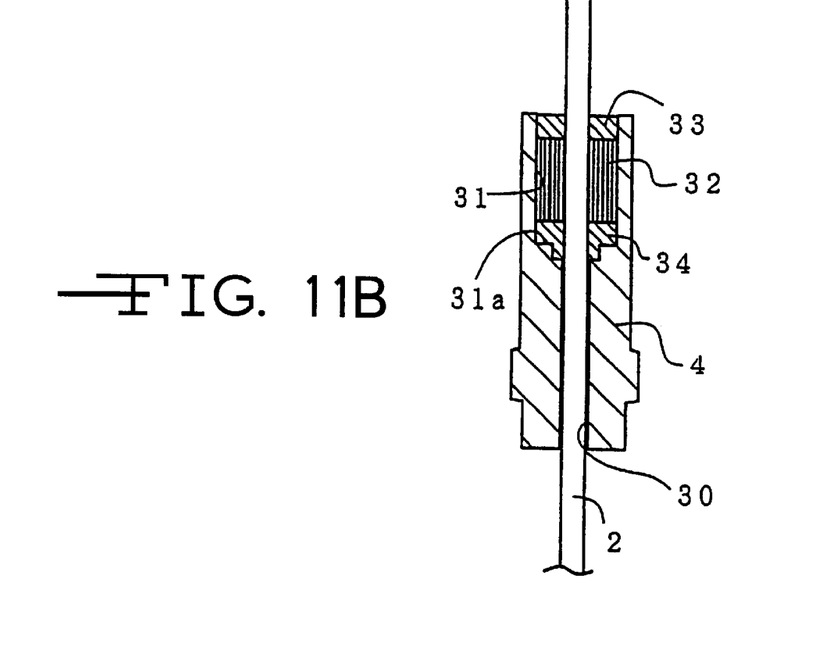
FIG. 11(b) is a full, sectional view showing a second modification of the cushion layer of the oxygen sensor of FIG. 6.

The reduced diameter portion 31a of the cushion layer 34 may assume a stepped form as shown in FIG. 11(b).

Figure 12:
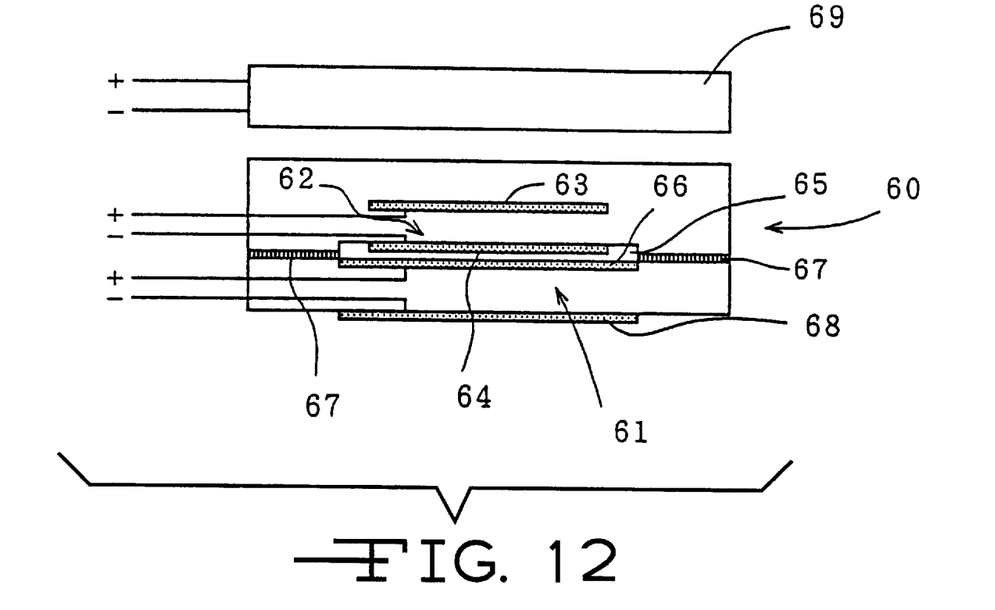
FIG. 12 is a schematic, sectional view of a full range oxygen sensor element which can be used as the ceramic element.

In the above embodiments, the gas sensor assumes the configuration of a λ sensor, which employs only an oxygen concentration cell element as a sensor element (ceramic element). However, the ceramic element may be of a different type. Examples of a sensor element of a different type will next be described. FIG. 12 schematically shows a full-range oxygen sensor element. In a ceramic element 60 of FIG. 12, an oxygen pump element 61 and an oxygen concentration cell element 62 are disposed facing each other while a measurement chamber 65 is formed therebetween. The oxygen pump element 61 and the oxygen concentration cell element 62 are each made of an oxygen-ion conductive solid electrolyte. Exhaust gas is introduced into the measurement chamber 65 through a porous diffusion hole 67 filled with porous ceramic. Reference numeral 69 denotes a heater for heating the oxygen pump element 61 and the oxygen concentration cell element 62. The oxygen concentration cell element 62 uses an electrode 63 embedded therein as an oxygen reference electrode. The concentration of oxygen contained in the measurement chamber 65 is determined based on an electromotive force which is generated by the concentration cell effect which arises between the electrode 63 and an electrode 64 facing the measurement chamber 65. An external power source (not illustrated) applies voltage to the oxygen pump element 61 via electrodes 66 and 68. Oxygen is pumped into or pumped out from the measurement chamber 65 according to the direction of the applied voltage, and the rate of pumping oxygen in or out is determined by the magnitude of the applied voltage. Based on the oxygen concentration of the measurement chamber 65 detected by the oxygen concentration cell element 62, a controller (not illustrated) controls the operation of the oxygen pump element 61 such that the oxygen concentration of the measurement chamber 65 is maintained at a constant level. At this time, the concentration of oxygen contained in the exhaust gas is determined based on a pump current which flows through the oxygen pump element 61.

Figure 13:
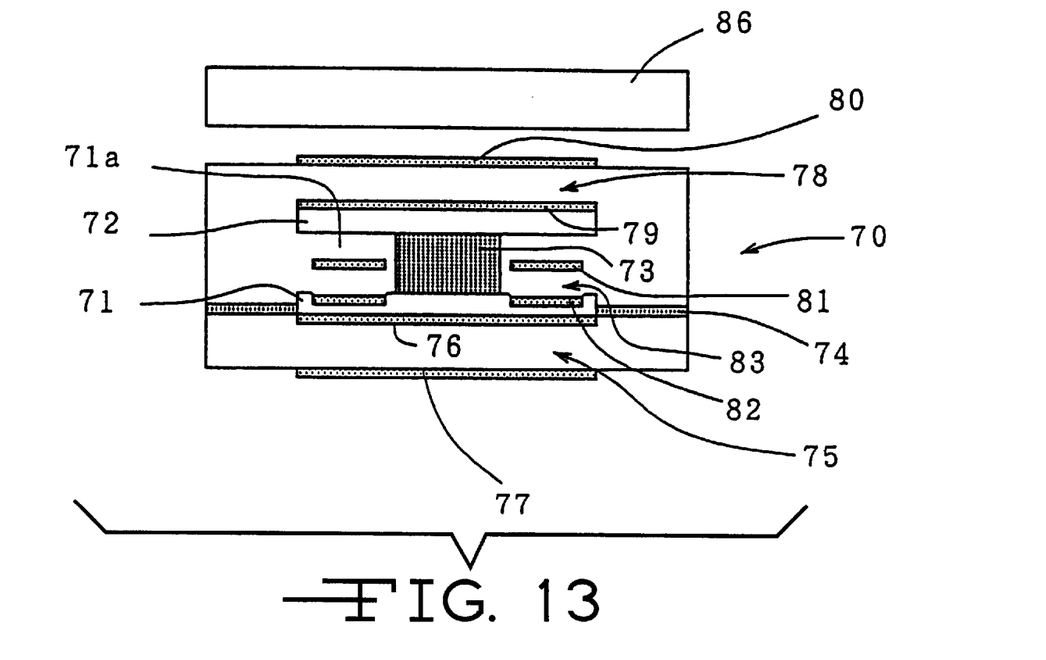
FIG. 13 is a schematic, sectional view of an NOx sensor element which can be used as the ceramic element.

FIG. 13 shows a ceramic element which assumes the form of a two-chamber $NO_x$ sensor element. A ceramic element 70 is made of an oxygen-ion conductive solid electrolyte such as $ZrO_2$. In the ceramic element 70, first and second measurement chambers 71 and 72 are formed such that a partition wall 71a is disposed therebetween. The partition wall 71a is made of porous ceramic. A second porous diffusion hole 73 is formed in the partition wall 71a and is filled with porous ceramic, so that communication is established between the first and second measurement chambers 71 and 72. The first measurement chamber 71 communicates with a surrounding atmosphere via a first porous diffusion hole 74. A first oxygen pump element 75 having electrodes 76 and 77 is provided for the first measurement chamber 71, and a second oxygen pump element 78 having electrodes 79 and 80 is provided for the second measurement chamber 72. The first oxygen pump element 75 and the second oxygen pump element 78 are disposed on opposite sides of the partition wall 71a. An oxygen concentration cell element 83 (having an oxygen reference electrode 81 formed within the partition wall 71a and a corresponding electrode 82 exposed to the first measurement chamber 71) for detecting the oxygen concentration in the first measurement chamber 71 is formed within the partition wall 71a. Numeral 86 denotes a heater for heating the first oxygen pump element 75, the second oxygen pump element 78, and the oxygen concentration cell element 83.

During operation, gas is introduced into the first measurement chamber 71 from the surrounding atmosphere via the first porous diffusion hole 74. Oxygen is pumped out from the introduced gas by means of the first oxygen pump element 75. The oxygen concentration cell element 83 detects the concentration of oxygen contained in the first measurement chamber 71. Based on the detected oxygen concentration, an unillustrated controller controls the operation of the first oxygen pump element 75 such that the oxygen concentration of the gas contained in the first measurement chamber 71 is maintained at such a constant level as not to cause decomposition of $NO_x$. The thus-oxygen-reduced gas enters the second measurement chamber 72 via the second porous diffusion hole 73. The second oxygen pump element 78 pumps out oxygen from the second measurement chamber 72 so as to completely decompose $NO_x$ and oxygen contained in the gas therewithin. At this time, based on a pump current which flows through the second oxygen pump element 78, the concentration of $NO_x$ contained in the gas of the surrounding atmosphere is determined.

We claim:

1. A gas sensor characterized in that
an insulator is disposed inside a metallic shell;
a sensor eleme nit too detecting a component of a gas to be measured is disposed inside said insulator;
a cavity is formed in said insulator to surround said sensor element, and a sealing material mainly made of glass is charged into the cavity in order to establish sealing between the inner surface of said insulator and the outer surface of said sensor element;
said sensor element has a rectangular cross section along a plane Q perpendicular to the axis of said sensor element; and a cavity defining inner surface of said insulator has a sectional profile that is determined by a method in which a line L1, that passes through the centroid G of the cross section of said sensor element and perpendicularly intersects the shorter sides of the cross section of said sensor element and a line L2 that passes through the centroid G of the cross section of said sensor element and perpendicularly intersects the longer sides of the cross section of said sensor element are drawn on the plane Q; intersections between the line L1 and the cavity defining inner surface are taken as P1 and P2, respectively; intersections between the line L1 and the cavity defining inner surface are taken as P3 and P4, respectively; while the longer of the distances GP1 and GP2 is used as a radius, a circle C centered at the centroid C is drawn; and the sectional profile of the cavity defining inner surface is determined such that both the points P3 and P4 fall within the circle C.

2. A gas sensor according to claim 1, characterized in that said cavity defining inner surface has a rectangular sectional profile such that the centroid of the sectional profile of said cavity defining inner surface substantially coincides with the centroid of the rectangular cross section of said sensor element and such that the sectional profile of said cavity-defining inner surface conforms to that of the cross section of said sensor element.

3. A gas sensor characterized in that an insulator is disposed inside a metallic shell;

a sensor element for detecting a component of a gas to be measured is disposed inside said insulator, said sensor element having a first configuration in cross section;

a cavity is formed in said insulator to surround said sensor element, and a sealing material mainly made of glass is charged into the cavity in order to establish sealing between the inner surface of said insulator and the outer surface of said sensor element, a cavity defining inner surface of said insulator has a second configuration in cross section larger than and conforming to said first configuration in cross section, said second configuration of said cavity defining inner surface is rectangular such that a centroid of the second configuration of said cavity defining inner surface substantially coincides with a centroid of a rectangular first configuration of said sensor element, and said cavity defining inner surface has an elliptical sectional profile such that the centroid of the sectional profile of said cavity defining inner surface substantially coincides with the centroid of the rectangular cross section of said sensor element and such that the major axis of the ellipse extends along the longitudinal direction of the cross section of said sensor element.

4. A gas sensor characterized in that an insulator is disposed inside a metallic shell;

a sensor element for detecting a component of a gas to be measured is disposed inside said insulator, said sensor element having a first, square configuration in cross section;

a cavity is formed in said insulator to surround said sensor element, and a sealing material mainly made of glass is charged into the cavity in order to establish sealing between the inner surface of said insulator and the outer surface of said sensor element; and whereas a cavity defining inner surface of said insulator has a second, square configuration in cross section larger than and conforming to said first, square configuration in cross section.

5. A gas sensor characterized in that an insulator is disposed inside a metallic shell;

a sensor element for detecting a component of a gas to be measured is disposed inside said insulator, said sensor element having a first, elliptical configuration in cross section;

a cavity is formed in said insulator to surround said sensor element, and a sealing material mainly made of glass is charged into the cavity in order to establish sealing between the inner surface of said insulator and the outer surface of said sensor element; and whereas a cavity defining inner surface of said insulator has a second, elliptical configuration in cross section larger than and conforming to said first, elliptical configuration in cross section.

* * * * *